United States Patent [19]
Dalbøge et al.

[11] Patent Number: 5,817,499
[45] Date of Patent: Oct. 6, 1998

[54] **DNA ENCODING AN ENZYME WITH ENDOGLUCANASE ACTIVITY FROM *TRICHODERMA HARZIANUM***

[75] Inventors: Henrik Dalbøge, Virum; Stephan Christgau, Gentofte; Lene Nonboe Andersen, Birkerød; Lene Venke Kofod, Ugerløse; Markus Sakari Kauppinen, Copenhagen, all of Denmark

[73] Assignee: Novo Nordisk A/S, Bagsvaerd, Denmark

[21] Appl. No.: 578,590

[22] PCT Filed: Jul. 5, 1994

[86] PCT No.: PCT/DK94/00275

§ 371 Date: Jan. 3, 1996

§ 102(e) Date: Jan. 3, 1996

[87] PCT Pub. No.: WO95/02043

PCT Pub. Date: Jan. 19, 1995

[30] Foreign Application Priority Data

Jul. 6, 1993 [DK] Denmark .................................. 0812/93

[51] Int. Cl.$^6$ ................................ C12N 5/10; C12N 9/24; C12N 15/56; C12N 21/02
[52] U.S. Cl. ................. 435/200; 435/254.11; 435/254.3; 435/320.1; 435/325; 536/23.2
[58] Field of Search ..................... 536/23.2; 435/320.1, 435/240.2, 252.3, 254.11, 209, 325, 200, 254.3

[56] References Cited

FOREIGN PATENT DOCUMENTS

WO 92/062209  4/1992  WIPO .

OTHER PUBLICATIONS

Sidhu et al., Folia Microbiol. 31:293–302, 1986.
Dialog Information Services, File 351, Derwent WPI, Dialog accession No. 003541017, WPI accession No. 82–89009E/42, (AGEN) Agency of Sci Tech: "High Yield Cellulase Prodn. By Culturing *Trichoderma harzianum* In Medium Contg. Enzyme Hydrolysis Prod. Of Caseinas Cellulase Prodn. Accelerator", JP 57146579 A 820910 8242 (Basic) (1982).
Dialog Information Services, File 3512, Derwent WPI, Dialog accession No. 003541016, WPI, Dialog accession No. 82–89008E/42, (AGEN) Agency of Ind Sci Tech: "Cellulase Prodn. By Culturing Microorganizm Of *Trichoderma Hazianum* Genus", JP 57146578 A 82910 8242 (Basic) (1982).
Patent Abstracts of Japan, vol. 16, No. 257, C–949, abstract of Japan, A, 40–58889 (Aizo Matsushiro), 25 Feb. 1992 (25 Feb. 1992).

*Primary Examiner*—Eric Grimes
*Attorney, Agent, or Firm*—Steve T. Zelson, Esq.; Valeta A. Gregg, Esq.

[57] ABSTRACT

DNA encoding an endoglucanase from *Trichoderma harzianum* is disclosed. The endoglucanase has activity toward mixed β-1,3-1,4 glucans and is especially useful in brewing processes.

11 Claims, No Drawings

DNA ENCODING AN ENZYME WITH ENDOGLUCANASE ACTIVITY FROM *TRICHODERMA HARZIANUM*

CROSS-REFERENCE TO RELATED APPLICATIONS

This application is a continuation of PCT/DK94/00275 filed Jul. 5, 1994, which is incorporated herein by reference.

FIELD OF INVENTION

The present invention relates to a DNA construct encoding an enzyme with endoglucanase activity, a method of producing the enzyme, an enzyme produced by the method, and an enzyme preparation containing the enzyme.

BACKGROUND OF THE INVENTION

Endoglucanases (EC no. 3.2.1.4) constitute a group of hydrolases, which catalyse endo hydrolysis of 1,4-β-D-glycosidic linkages in cellulose, cellulose derivatives (such as carboxy methyl cellulose and hydroxy ethyl cellulose), lichenin, β-1,4 bonds in mixed β-1,3 glucans such as cereal β-D-glucans or xyloglucans and other plant material containing cellulosic parts. The authorized name is endo-1,4-β-D-glucan 4-glucano hydrolase, but the abbreviated term endoglucanase is used in the present specification. Reference can be made to R. F. Gould, "Cellulases and their Application", Advances in Chemistry Series 55, American Chemical Society (1969), T. M. Wood, "Properties and Mode of Action of Cellulases", in Biotechnology and Bioengineering Symposium, no. 5, John Wiley, 111–137 (1975), Y.-H. Lee and L. T. Fan, "Properties and Mode of Action of Cellulose", Advances in Biochemical engineering 17, 101–129 (1980), J. Goksøyr and J. Eriksen, "Cellulases" in A. H. Rouse, Microbial Enzymes and Bioconversions, Academic Press, 283–330 (1980), T.-M. Enveri, "Microbial Cellulases" in W. M. Fogarty, Microbial Enzymes and Biotechnology, Applied Science Publishers, 183–224 (1983), Béguin, P. and Aubert, J-P., "The biological degradation of cellulose", FEMS Microbiology Reviews 13 (1994) 25–58. Celluloses are found in connection with many gums and they are components of cell walls in e.g. fruits, vegetables and cereals. Several cellulolytic genes from the genus Trichoderma have been cloned and characterized by Shoemaker et al. (1983), Teeri et al. (1983), Chen et al. (1987), Teeri et al. (1987), Penttilä et al. (1986), van Arsdell et al. (1987), Saloheimo et al. (1988), Barnett et al. (1991) and González et al. (1992).

The object of the invention is to provide a novel endoglucanase and a method for producing the endoglucanase in a better yield and higher purity than hitherto possible, as well as the use of the endoglucanase either alone or in combination with other enzymes for the degradation of plant cell wall tissue. Also it is the object of the invention to provide novel products, wherein the proportion of the endo-β-1,4-glucanase is increased relative to the proportion in the original product.

SUMMARY OF THE INVENTION

The present inventors have now surprisingly isolated a novel DNA sequence from a strain of *Trichoderma harzianum*, which encodes an endoglucanase enzyme the deduced amino acid sequence of which has been found to be without homology to any of the above mentioned known endoglucanases or any other known enzymes.

Accordingly, in a first aspect the invention relates to a DNA construct comprising a DNA sequence encoding an enzyme with endoglucanase activity, which DNA sequence comprises the DNA sequence shown in SEQ ID No. 1 or an analogous sequence thereof being at least 70% homologous to the DNA sequence shown in SEQ ID No. 1.

The DNA sequence shown in SEQ ID No. 1 encodes an enzyme which in the following disclosure is referred to as Endoglucanase I.

In further aspects the invention relates to an expression vector harbouring a DNA construct of the invention, a cell comprising the DNA construct or expression vector and a method of producing an enzyme with endoglucanase activity which method comprises culturing said cell under conditions permitting the production of the enzyme, and recovering the enzyme from the culture.

In a still further aspect the invention relates to an enzyme with endoglucanase activity, which enzyme a) is encoded by a DNA construct of the invention as defined above, b) produced by the method of the invention, and/or c) is immunologically reactive with an antibody raised against a purified endoglucanase encoded by the DNA sequence shown in SEQ ID No. 1 and derived from *Trichoderma harzianum*, CBS 243.71.

In the present context, the term "derived from" is intended not only to indicate an endoglucanase produced by strain CBS 243.71, but also an endoglucanase encoded by a DNA sequence isolated from strain CBS 243.71 and produced in a host organism transformed with said DNA sequence.

The enzyme encoded by an analogous DNA sequence is preferably at least 70% homologous to the enzyme encoded by the DNA sequence shown in SEQ ID No. 1, such as at least 80% and more preferably at least 90% homologous.

Endoglucanase I described herein is a preferred example of an enzyme of the invention. By the present invention it is posssible to produce the enzyme in a highly purified form, i.e. greater than 75% pure, more preferably greater than 90% pure as determined by SDS-PAGE using the procedure described by Laemmli, 1970 and Christgau, 1991.

In final aspects the invention relates to an enzyme preparation comprising an enzyme of the invention and the use of the enzyme or enzyme preparation for various purposes in which modification or degradation of plant cell wall containing material is desirable.

In a still further aspect, the present invention relates to an enzyme preparation useful for the degradation of plant cell wall components, said preparation being enriched in an enzyme exhibiting endoglucanase activity as described above.

DETAILED DESCRIPTION OF THE INVENTION

In the present context the term "analogue" used to define the DNA construct of the invention is understood to include any DNA sequence which encodes an enzyme with endoglucanase activity and which is at least 70% homologous to the DNA sequence shown in SEQ ID No. 1. The analogous DNA sequence is preferably a DNA sequence which hybridizes to the same probe as the DNA coding for the endoglucanase enzyme under the following conditions: presoaking in 5×SSC and prehybridizing for 1 h at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~40° C. followed by washing three times in 2×SSC, 0.2% SDS at 40° C. for 30 minutes. The analogous DNA sequence is preferably at least 80% homologous to the sequence shown in SEQ ID No. 1, preferably at least 90% and most preferably at least 95% homologous to said sequence.

The term is intended to include modifications of the DNA sequence shown in SEQ ID No. 1, such as nucleotide substitutions which do not give rise to another amino acid sequence of the endoglucanase but which correspond to the codon usage of the host organism into which the DNA construct is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

Furthermore, it is preferred that the endoglucanase encoded by the analogous DNA sequence is immunologically crossreactive with an antibody raised against the purified endoglucanase encoded by the DNA sequence shown in SEQ ID No. 1.

The nucleotide probe with which the analogue of the DNA sequence shown in SEQ ID No. 1 can hybridize may, e.g. be prepared on the basis of any of the following DNA sequences or any combination thereof:

(a) CTTGCTCTGA CGGTTGCGAA(SEQ ID NO:2)
(b) TCCTTGTATC CCACTTCTAA(SEQ ID NO:3)
(c) ACGATATCAA AACAACACAT(SEQ ID NO:4)
(d) TCATCACCAA GATGCATTTC(SEQ ID NO:5)
(e) CAATCTCTCA ACCTCTTGGC(SEQ ID NO:6)
(f) CCTGGCCATC TCTTCGGTCA(SEQ ID NO:7)
(g) CGGCCACTCT CTCCCCAAAC(SEQ ID NO:8)
(h) ATCCCCGGCA TGAACCTCGT(SEQ ID NO:9)
(i) CTGGCAAGAG ACGTTTGTTG(SEQ ID NO:10)
(j) GCGAGCAAGG CGACATGGTT(SEQ ID NO:11)
(k) GACCTCACCC AGTGGACCGT(SEQ ID NO:12)
(l) CGTCACCGAC CTCCACAACA(SEQ ID NO:13)
(m) ACCAGGAGCT CGAGACTTAC(SEQ ID NO:14)
(n) ACCCAGTCCG ATTCCAACAT(SEQ ID NO:15)
(o) GCAGCTCTCC GGCGGCCA(SEQ ID NO:16)
(p) GACTCTCCAG CTCGTCCCTC(SEQ ID NO:17)
(q) AACAGGCTGA GTGCGGCGAA(SEQ ID NO:18)
(r) TGGACCTCCT CCCGCATTGAA(SEQ ID NO:19)
(s) TCATCAGTGC TGGACTCATC(SEQ ID NO:20)
(t) TCCCGGCAAG ACATGACAAG TTCAA(SEQ ID NO:21)

These sequences constitute partial sequences of the DNA sequence shown in SEQ ID No. 1 or analogues of such sequences.

The DNA sequence of the invention encoding an enzyme with endoglucanase activity may be isolated by a general method involving cloning, in suitable vectors, a DNA library from Trichoderma sp., transforming suitable yeast host cells with said vectors, culturing the host cells under suitable conditions to express any enzyme of interest encoded by a clone in the DNA library, and screening for positive clones by determining any endoglucanase activity of the enzyme produced by such clones.

A more detailed description of this screening method is given in Example 1 below and in WO 93/11249, the contents of which is hereby incorporated by reference.

The DNA sequence coding for the enzyme may for instance be isolated by screening a cDNA library of *Trichoderma harzianum*, e.g strain CBS 243.71, publicly available from Centraalbureau voor Schimmelcultures, and selecting for clones expressing the appropriate enzyme activity (i.e. endoglucanase activity as defined by the ability of the enzyme to hydrolyse β-1,3 and/or β-1,4 bonds between two glucose molecules in polymers containing glucose (e.g. cellulose, cereal β-glucans or xyloglucans)). The appropriate DNA sequence may then be isolated from the clone by standard procedures, e.g. as described in Example 1. It is expected that a DNA sequence coding for a homologous enzyme may be derived by similarly screening a cDNA library of another microorganism such as a yeast or a fungus, in particular a strain of an *Aspergillus sp.*, a *Trichoderma sp.*, e.g. a strain of *Trichoderma harzianum, Trichoderma longibrachiatum, Trichoderma koningii* or *Trichoderma reesei, Trichoderma viridae*, a *Penicillium sp.*, a *Fusarium sp.* or a *Humicola sp.*

Alternatively, the DNA coding for an endoglucanase of the invention may, in accordance with well-known procedures, conveniently be isolated from DNA from any of the above mentioned organisms by use of oligonucleotide probes, such as 20mer probes, prepared on the basis of a DNA sequence shown in SEQ ID No. 1. For instance, a suitable oligonucleotide probe may, e.g., be prepared on the basis of any of the partial nucleotide sequences a)–t) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus or Trichoderma, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum,* a strain of *Schizosaccharomyces sp.,* such as *Schizosaccharomyces pombe,* a strain of *Hansenula sp. Pichia sp., Yarrowia sp.* such as *Yarrowia lipolytica,* or *Kluyveromyces sp.* such as *Kluyveromyces lactis.*

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In a still further aspect, the present invention relates to an enzyme preparation useful for the degradation or modification plant cell wall containing materials, said preparation being enriched in an enzyme with endoglucanase activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast or Celluzyme (all available from Novo Nordisk A/S). In the present context, the term "enriched" is intended to indicate that the endoglucanase activity of the enzyme preparation has been increased, e.g. with an enrichment factor of at least 1.1, conveniently due to addition of an enzyme of the invention prepared by the method described above.

Alternatively, the enzyme preparation enriched in an enzyme with endoglucanase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to the endoglucanase of the invention, contain one or more other plant cell wall degrading enzymes, for instance those with cellulytic, xylanolytic or pectinolytic activities such as xylanase, arabinanase, galactanase, rhamnogalacturonase, pectin acetylesterase, galactanase, polygalacturonase, pectin lyase, pectate lyase, endoglucanase (e.g. of another specificity than the endo-glucanase disclosed herein) or pectin methylesterase.

The additional enzyme(s) may be producible by means of a microorganism belonging to the genus Aspergillus, preferably *Aspergillus niger, Aspergillus aculeatus, Aspergillus awamori* or *Aspergillus oryzae.*

The endoglucanase according to the invention may also be produced essentially free from other plant cell wall degrading enzyme. This makes it possible to use the enzyme alone or together with other monocomponent enzymes to give the optimal combination of enzymes for a particular application. It is thereby possible to design enzyme combinations, which only degrade specific parts of the plant cell. This specific degradation has not previously been possible to obtain with commercially available cellulase, hemicellulase and/or pectinase preparations.

The endoglucanase of the invention has been found to have a high specificity towards β-glucan.

This activity towards mixed β-1,3-1,4 glucans makes the endoglucanase and homologues thereof useful for brewing purposes as the enzymes degrades the barley β-glucan and thereby reduces the viscosity and improves the filterability of the wort. In brewing the high specificity for β-glucans is an advantage as compared to other endoglucanases as the viscosity caused by β-glucan can be reduced without simultaneous degradation of the cellulose structures which are essential for the filterability of the wort where brewers spent grains act as filter-aid. Furthermore, the activity towards mixed β-1,3-1,4 glucans makes the enzyme useful for processing of or for addition to food or feed to improve the feed-uptake and/or digestibility. Furthermore, the endoglucanase may be used to improve the quality of baked products or other cereal products.

The endoglucanase of the invention may also be used to produce oligosaccharides from e.g. plant material with mixed β-1,3-1,4 glucan. The resulting oligosaccharides may be used as bulking agents in e.g. food.

Furthermore, the endoglucanase may be used for extraction of aromatic compounds from plant materials.

For the above uses, the dosage of the enzyme preparation of the invention and other conditions under which the preparation is used may be determined on the basis of methods known in the art.

The invention is described in further detail in the following examples which are not in any way intended to limit the scope of the invention as claimed.

MATERIALS AND METHODS

Donor organism: mRNA was isolated from *Trichoderma harzianum,* CBS 243.71, grown in a maize grits-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prcl::HIS3; prbl:: LEU2; cir+).

Plasmids: The expression plasmid pYHD17 containing the yeast TPI promoter was prepared from the commercially available plasmid pYES II (Invitrogen). The plasmid and the construction thereof is further described in WO 93/11249, the contents of which is hereby incorporated by reference.

The Aspergillus expression vector pHD414 is a derivative of the plasmid p775 (described in EP 238 023). The construction of pHDA14 is further described in Wo 93/11249. pHD414 contains the *A. niger* glucoamylase terminator and the *A. oryzae* TAKA amylase promoter.

Extraction of total RNA: The total RNA was prepared by extraction with guanidinium thiocyanate followed by ultracentrifugation through a 5.7M CsCl cushion essentially as described by Chirgwin et al., 1979 and in WO 93/11249.

Isolation of poly(A)$^+$RNA: The poly(A)$^+$RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1M NaCl, 1 mM EDTA, 0.1% SDS), followed by elution of the poly(A)+RNA with 3 vols of elution buffer (10 mM Tris-Cl, pH 7.6, 1 mM EDTA, 0.05% SDS) preheated to +65° C., by collecting 500 μl fractions. The $OD_{260}$ was read for each collected fraction, and the mRNA containing fractions were pooled and ethanol precipitated at −20° C. for 12 h. The poly(A)$^+$ RNA was collected by centrifugation, resuspended in DEPC-DIW and stored in 5–10 μg aliquots at −80° C.

Northern blot analysis: The poly(A)$^+$ RNAs (5 μg/sample) from various mycelia were electrophoresed in 1.2% agarose-2.2M formaldehyde gels (Sambrook et al., 1989) and blotted to nylon membranes (Hybond-N, Amersham) with 10×SSC (Sambrook et al., 1989) as transfer buffer. A random-primed (Feinberg & Vogelstein, 1983) $^{32}$P-labeled cDNA probe for mutanase from $T.$ $harzianum$ was used in individual hybridizations (a 350 bp PCR generated fragment). Northern hybridizations were carried out in 5×SSC (Sambrook et al., 1989), 5×Denhardt's solution (Sambrook et al., 1989), 0.5% SDS (w/v) and 100 μg/ml denatured salmon sperm DNA with a probe concentration of ca. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2×15 min). Autoradiography at −80° C. for 12 h. The RNA ladder from Bethesda Research Laboratories was used as a size marker.

cDNA Synthesis: First strand synthesis: Double-stranded cDNA was synthesized from 5 μg of $T.$ $harzianum$ poly(A)$^+$ RNA by the RNase H method (Gubler & Hoffman 1983, Sambrook et al., 1989) using the hairpin modification. The poly(A)$^+$RNA (5 μg in 5 μl of DEPC-treated water) was heated at 70° C. for 8 min., quenched on ice, and combined in a final volume of 50 μl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 μg of oligo(dT)$_{12–18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second strand synthesis: After synthesis 30 μl of 10 mM Tris-Cl, pH 7.5, 1 mM EDTA was added, and the mRNA:cDNA hybrids were ethanol precipitated for 12 h at −20° C. by addition of 40 μg glycogen carrier (Boehringer Mannheim) 0.2 vols 10M $NH_4Ac$ and 2.5 vols 96% EtOH. The hybrids were recovered by centrifugation, washed in 70% EtOH, air dried and resuspended in 250 μl of second strand buffer (20 mM Tris-Cl, pH 7.4, 90 mM KCl, 4.6 mM MgCl2, 10 mM $(NH_4)_2SO_4$, 16 μM $\beta NAD^+$) containing 100 μM each dNTP, 44 units of $E.$ $coli$ DNA polymerase I (Amersham), 6.25 units of RNase H (Bethesda Research Laboratories) and 10.5 units of $E.$ $coli$ DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) CDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and is resuspended in 30 μl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 μl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds CDNA was blunt-ended with T4 DNA polymerase in 50 al of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection: After the fill-in reaction the cDNA was ligated to non-palindromic BstX I adaptors (1 μg/μl, Invitrogen) in 30 μl of ligation buffer (50 mM Tris-Cl, pH 7.8, 10 mM MgCl2, 10 mM DTT, 1 mM ATP, 25 μg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The CDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of CDNA libraries: The adapted, ds cDNA was recovered by centrifugation, washed in 70% EtOH and resuspended in 25 ml DIW. Prior to large-scale library ligation, four test ligations were carried out in 10 μl of ligation buffer (same as above) each containing 1 μl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either pYES 2.0 vector (Invitrogen) or pYHD17). The ligation reactions were performed by incubation at +16° C. for 12 h, heated at 70° C. for 5 min, and 1 μl of each ligation electroporated (200 Ω, 2.5 kV, 25 μF) to 40 μl competent $E.$ $coli$ 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h , 50 μl plated on LB+ampicillin plates (100 μg/ml) and grown at +37° C. for 12 h.

Using the optimal conditions a large-scale ligation was set up in 40 μl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 μl DIW. One μl aliquots were transformed into electrocompetent $E.$ $coli$ 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent S. cerevisiae JG 169 cells (OD600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80 μl aliquots were plated on SC+glucose−uracil to give 250–500 c.f.u./plate and incubated at 30° C. for 3–5 days.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH 7.0. Centrifugation is performed for 15 minutes at 100 g and the protoplasts are collected from the top of the $MgSO_4$ cushion. 2 volumes of STC (1.2M sorbitol, 10 mM Tris-HCl, pH 7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove in Biochem.Biophys.Acta 113 (1966) 51–56) containing 1.0M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Immunological cross-reactivity: Antibodies to be used in determining immunological cross-reactivity may be prepared by use of a purified endoglucanase. More specifically, antiserum against the endoglucanase may be raised by immunizing rabbits (or other rodents) according to the procedure described by N. Axelsen et al. in: *A Manual of Quantitative Immunoelectrophoresis*. Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

Media

YPD: 10 g yeast extract, 20 g peptone, $H_2O$ to 810 ml. Autoclaved, 90 ml 20% glucose (sterile filtered) added.

YPG-agar: 25 g/l Bactoagar, 15 g/l glucose, 5 g/l $K_2PO_4$, 0.5 g/l $MgSO_4$-$7H_2O$, pH adjusted to 5.0. Autoclaved.

10×Basal salt: 66.8 g yeast nitrogen base, 100 g succinic acid, 60 g NaOH, $H_2O$ and 1000 ml, sterile filtered.

SC-URA: 90 ml 10×Basal salt, 22.5 ml 20% casamino acids, 9 ml 1% tryptophane, $H_2O$ and 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

FG-4-Agar: 35 g/l agar, 30 g/l Soy bean meal, 15 g/l maltodextrin (Glucidex 6), 5 g/l Bacto pepton, pH 7. Autoclaved 40 min at 121° C.

FG-4 medium: 30 g/l Soy bean meal, 15 g/l maltodextrin (Glucidex 6), 5 g/l Bacto pepton. Autoclaved 40 min at 121° C.

AZCL β-glucan (Megazyme, Australia).

AZCL xyloglucan (Megazyme, Australia).

AZCL HE cellulose (Megazyme, Australia).

EXAMPLE 1

A library from *Trichoderma harzianum* CBS 243.71 consisting of approx. $10^6$ individual clones in 50 pools was constructed in *E. coli* as previously described.

DNA was isolated from 20 individual clones from the library and subjected to analysis for CDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of the replica plates contained 0.1% AZCL β-glucan. These plates were incubated for 3–7 days at 30° C. Endoglucanase positive colonies were identified as colonies surrounded by a blue halo.

Cells from enzyme-positive colonies were spread for single colony isolation on agar, and an enzyme-producing single colony was identified and selected by the above described method.

The isolated yeast clones were simultaneously tested on agar plates containing AZCL β-glucan, AZCL xyloglucan or AZCL HE cellulose, but found positive only on AZCL β-glucan.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The DNA sequence of the enzyme gene is shown in SEQ ID No. 1.

EXAMPLE 2

Isolation of DNA

An isolate was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 μl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 μl 5M KOAC was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 μl TE (Tris-EDTA) and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μl/ml.

The DNA was transformed into E. coli by standard procedures. Two E. coil colonies were isolated and analysed with the restriction enzymes HindIII and XbaI which excised the DNA insert.

The DNA sequences of several of the positive clones were determined. The DNA sequence of the endoglucanase gene of the invention is shown in SEQ ID No. 1.

EXAMPLE 3

Expression of Endoglucanase

In order to express the endoglucanase the DNA is digested with HindIII/XbaI, size fractionated on gel, and a fragment corresponding to the endoglucanase gene is purified. The gene is subsequently ligated to HindIII/XbaI digested pHD414 resulting in the plasmid pAIBG I.

After amplification of the DNA in E. coli the plasmid pAIBG I is transformed into Aspergillus oryzae as described above.

Each of the transformants was inoculated on FG agar in the centre of a Petri dish. After 4 days of incubation at 30° C., 4 mm diameter plugs were removed by means of a corkscrew. The plugs were embedded in a β-glucan overlayer gel containing 0.1% AZCL β-glucan and 1% agarose in a buffer with an appropriate pH, and incubated overnight at 30° C. The endoglucanase activity was identified as described above. Some of the transformants had halos which were significantly larger than the A. oryzae background. This demonstrates expression of endoglucanase in A. oryzae.

REFERENCES

Aviv, H. & Leder, P. 1972. Proc. Natl. Acad. Sci. U.S.A. 69:1408–1412.

Becker, D. M. & Guarante, L. 1991. Methods Enzymol. 194:182–187.

Chirgwin, J. M., Przybyla, A. E., MacDonald, R. J. & Rutter, W. J. 1979. Biochemistry 18:5294–5299.

Gubler, U. & Hoffman, B. J. 1983. Gene 25:263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74:5463–5467.

Barnett, C. C. et al. (1991). BioTechnology 9:562–567

Chen, C. et al. (1987). BioTechnology 5:274–278

Penttilä, M. et al. (1986). Gene 45:253–263.

Saloheimo, M. et al. (1988). Gene 63:11–21.

Shoemaker, S. et al. (1983). BioTechnology 1:691–696.

Teeri, T. et al. (1983). BioTechnology 1:696–699.

Teeri, T. et al. (1987). Gene 51:43–52.

van Arsdell, J. N. et al. (1987). BioTechnology 5:60–64.

Christgau, S., et al., 1991, "Pancreatic β-cells express two autoantigenic forms of glutamic acid decarboxylase, a 65 kDa hydrophilic form and a 64 kDa amphiphilic form which can be both membrane-bound and soluble.". J. Biol. Chem., 266, p. 21157–212664.

Laemmli, U. K., 1970, "Cleavage of structural proteins during the assembly of the head of bacteriophage T4"., Nature, 227, p. 680–685.

Gonzales, R. et al, 1992, "Cloning, sequence analysis and yeast expression of the egl1 gene from Trichoderma longibrachiatum, Appl. Microbiol. Biotechnol. 38:370–375.

Béguin, P. and Aubert, J.-P., 1994, "The biological degradation of cellulose", FEMS Microbiology Reviews, 1994, 13:25–28.

We claim:

1. An isolated DNA sequence encoding an enzyme with endoglucanase activity derived from *Trichoderma harzianum*, which DNA sequence comprises the DNA sequence of SEQ ID NO:1 or a DNA sequence which hybridizes to the DNA sequence of SEQ ID NO:1 under the following conditions: presoaking in 5×SSC and prehybridizing for one hour at about 40° C. in a solution of S5×SSC, 5×Denhardt's solution, 50 mM sodium phosphate, pH 6.8, and 50 μg of denatured sonicated calf thymus DNA, followed by hybridization in the same solution supplemented with 50 μCi $^{32}$P-dCTP labelled probe for 18 hours at about 40° C. followed by washing three times in 2×SSC, 0.2% SDS at 40° C. for 30 minutes.

2. The DNA sequence of claim 1, wherein the DNA sequence is isolated from *Trichodenna harzianum*, CBS 243.71.

3. A recombinant expression vector comprising the DNA sequence of claim 1.

4. A cell comprising the DNA sequence of claim 1.

5. The cell of claim 4, wherein the cell is a eukaryotic cell selected from the group consisting of a yeast cell or a filamentous fungal cell.

6. The cell of claim 5, wherein the cell belongs to a strain of Aspergillus.

7. The cell of claim 6, wherein the Aspergillus strain is *Aspergillus niger* or *Aspergillus oryzae*.

8. A method of producing an enzyme with endoglucanase activity, the method comprising culturing a cell according to claim 4 under conditions permitting the production of the enzyme, and recovering the enzyme from the culture.

9. An enzyme with endoglucanase activity, wherein said enzyme is encoded by the DNA sequence of claim 1.

10. An enzyme preparation useful for the degradation of plant cell wall components, said preparation comprising an enzyme exhibiting endoglucanase activity according to claim 9.

11. The preparation according to claim 10, which additionally comprises a galactanase, xylanase, arabinanase, pectin acetyl esterase, polygalacturonase, rhamnogalacturonase, pectin lyase, pectate lyase, endoglucanase or pectin methylesterase.

\* \* \* \* \*

UNITED STATES PATENT AND TRADEMARK OFFICE
CERTIFICATE OF CORRECTION

PATENT NO. : 5,817,499
DATED : October 6, 1998
INVENTOR(S) : Dalboge, et. al.

It is certified that error appears in the above-identified patent and that said Letters Patent is hereby corrected as shown below:

Col. 21, line 48, claim 1, delete "S5xSSC" and insert --5xSSC--.
Col. 21, line 56, claim 2, delete "Trichodenna" and insert --Trichoderma--

Signed and Sealed this

Twenty-seventh Day of February, 2001

Attest:

NICHOLAS P. GODICI

Attesting Officer        Acting Director of the United States Patent and Trademark Office

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CTTTGATACC   CTTTTTTTTC   TTTTCAAACT   TCATTCCCTT   TCTCAGGCCT   GTGGCCGTTT       60
ACCTTCCTTT   CGCTGGTCGA   TTCTGCGCAC   TCCTTTTCTT   GTTACTGTTG   AACAGGCAAA      120
ACACCAAAAA   ACAAAACAGA   CAGACAGACA   CTCCTTTGTC   CAAGTCTAGA   TATTCATTCC      180
CTCAGTTGAT   CGTGATTCGC   AACCGTCAGA   GCAAGACTCT   CTCTTCTGAT   ACAGATCCTT      240
GTATCCCACT   TCTAAACGAT   ATCAAAACAA   CACATTCATC   ACCAAGATGC   ATTTCCAATC      300
TCTCAACCTC   TTGGCCCTGG   CCATCTCTTC   GGTCACGGGC   ACTCTCTCCC   CAAACATCCC      360
CGGCATGAAC   CTCGTCTGGC   AAGAGACGTT   TGTTGGCGAG   CAAGGCGACA   TGGTTGACCT      420
CACCCAGTGG   ACCGTCGTCA   CCGACCTCCA   CAACAACCAG   GAGCTCGAGA   CTTACACCCA      480
GTCCGATTCC   AACATGCAGC   TCTCCGGCGG   CCAGACTCTC   CAGCTCGTCC   CTCAACAGGC      540
TGAGTCCGGC   GAATGGACCT   CCTCCCGCAT   TGAATCCATC   CAGTCCTGGA   CTCCATCTCC      600
CGGCAAGACC   ATGCAAGTTC   AAGCTGCTCT   GCGTGGCGGC   TCCAGCCCCC   TCGACACCAA      660
GCAAGGCATG   TGGTCCGCCT   TCTGGATGCT   CGGCGACTCC   ATGCGTCACG   GCACTCCCTG      720
GCCGCTCTGC   GGAGAGCTCG   ACATCTTTGA   GCAGATCAAC   GGCCAGTTGA   CCGGCTACGG      780
CACCGCACAC   TGCGACCACA   CCGGCGGCGG   TGCGTGCAAC   GAGCCCTCGG   GACTGGGCCA      840
GAGCATTCCC   ATTCCCCAGG   ACGACGACTT   CCACACCTGG   GCTCTCAAGA   TCAACCGCTC      900
GTCCAACAAC   TGGCAGACGG   AGACGATCGA   GTGGTACCTC   GACGGCACGC   TCTTCCACAC      960
CCTTGTCGGT   GCTCAGTTTG   GCGACGAGGG   TCTTTGGGCA   ACGCTTGCGC   ACTCTCCAAT     1020
GTACATCATT   CTTAACCTTG   CTGTTGGTGG   TACATGGCCC   GGTGACCCTA   ACGAGGCGAC     1080
TCTGCCCGGC   TGGGGTAACA   TGTTTGAAGT   TCAATATGTT   GCCGTCTACT   CCTCCTAAGG     1140
GGGGCTAGCT   CGATGGAGAG   GGAGAGGATG   ATATAAAAAA   GAAAAGATG   GAGGGGAAAA     1200
AAAATAAAAG   GAAATTTTGG   ATTTGGGTAG   ATATGGTAGA   AGGCGCTTTT   ATGATGCACA     1260
TGTCATGACA   AACATGTCCC   TCCGTGGGAC   CCCATTTTGA   TTCACTGTAT   ATATATTTAA     1320
GATACCTTAT   GACGACGACT   GTTATGACTC   TCCAACCACC   AAAAAAAA                    1368
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
CTTGCTCTGA   CGGTTGCGAA                                                           20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCCTTGTATC CCACTTCTAA     20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

ACGATATCAA AACAACACAT     20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TCATCACCAA GATGCATTTC     20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CAATCTCTCA ACCTCTTGGC     20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCTGGCCATC TCTTCGGTCA     20

( 2 ) INFORMATION FOR SEQ ID NO:8:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

CGGCCACTCT CTCCCCAAAC 20

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

ATCCCCGGCA TGAACCTCGT 20

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

CTGGCAAGAG ACGTTTGTTG 20

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

GCGAGCAAGG CGACATGGTT 20

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

GACCTCACCC AGTGGACCGT 20

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

CGTCACCGAC CTCCACAACA 20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

ACCAGGAGCT CGAGACTTAC 20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

ACCCAGTCCG ATTCCAACAT 20

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GCAGCTCTCC GGCGGCCA 18

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GACTCTCCAG CTCGTCCCTC 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

AACAGGCTGA GTGCGGCGAA 20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TGGACCTCCT CCCGCATTGA A     21

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TCATCAGTGC TGGACTCATC     20

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TCCCGGCAAG ACATGACAAG TTCAA     25